United States Patent [19]

Thomas et al.

[11] Patent Number: 5,554,115
[45] Date of Patent: Sep. 10, 1996

[54] SENSOR FOR MEASURING PRESSURES IN A CASSETTE PUMP PROXIMAL AND DISTAL TO A PUMPING CHAMBER

[75] Inventors: V. Stanton Thomas, Palo Alto; Peter A. Holst, Castro Valley, both of Calif.

[73] Assignee: Abbott Laboratories, Abbott Park, Ill.

[21] Appl. No.: 418,752

[22] Filed: Apr. 7, 1995

[51] Int. Cl.$^6$ .................................................. A61M 31/00
[52] U.S. Cl. ...................... 604/65; 604/67; 128/DIG. 12; 128/DIG. 13
[58] Field of Search ............................... 604/65, 67, 118, 604/132; 128/DIG. 12, DIG. 13

[56] References Cited

U.S. PATENT DOCUMENTS

| | | | |
|---|---|---|---|
| 4,617,014 | 10/1986 | Cannon et al. | 604/67 |
| 4,950,244 | 8/1990 | Fellingham et al. | 604/118 |
| 5,103,211 | 4/1992 | Daoud et al. | 128/DIG. 13 X |
| 5,217,355 | 6/1993 | Hyman et al. | 417/474 |

*Primary Examiner*—Randall L. Green
*Assistant Examiner*—A. T. Nguyen
*Attorney, Agent, or Firm*—Ronald M. Anderson

[57] ABSTRACT

A pressure sensor (10) that responds to stress introduced into a pair of cantilevered beams (42, 44), to sense pressures at two measurement points in a cassette (80). The pressure sensor includes a base (12) on which the cantilevered beams are mounted. The base also supports two S-shaped flat springs (34, 36) mounted in spaced-apart, parallel array. Pins (28, 29) supported by the S-shaped flat springs each contact a free end of a different one of the cantilevered beams. The pins transfer a force from an elastomeric membrane (86). This force is developed by fluid pressure acting on the elastomeric membrane in a fluid passage of a cassette used for pumping fluid. The pins transmit the force to the free ends of the cantilevered beams as an applied stress. Strain gauges (58, 60) that are fixed to the cantilevered beams each respond by producing a signal indicative of fluid pressure. This configuration senses a proximal and a distal fluid pressure in the cassette, with substantially zero displacement of the elastomeric membrane, thereby minimizing errors that would otherwise arise due to variations in the stiffness of the elastomeric membrane with displacement and providing a short response time to changes in pressure.

21 Claims, 3 Drawing Sheets

SENSOR FOR MEASURING PRESSURES IN A CASSETTE PUMP PROXIMAL AND DISTAL TO A PUMPING CHAMBER

FIELD OF THE INVENTION

The present invention generally pertains to a sensor for monitoring fluid pressure, and more specifically, to a sensor that uses a strain gauge to sense pressure.

BACKGROUND OF THE INVENTION

There are many applications in which it is necessary to monitor fluid pressure to control a process. In medical technology, for example, pumps used to administer fluid to a patient typically include a pressure sensor for measuring the pressure of the fluid at the outlet of the pump. One such pump accepts a disposable plastic cassette that is fitted into engagement with an appropriate driver that is selectively actuated to controllably deliver medicinal fluids intravenously to a patient. The cassette comprises a plastic shell or housing made by joining a front section to a back section. A thin elastomeric sheet is encapsulated between the two sections. Fluid flows from an inlet port into a pumping chamber defined by a concave depression in one of the sections through passages formed in the housing, and a piston actuated by the pump driver displaces the elastomeric membrane to force the fluid from the pumping chamber toward an outlet port under pressure. A pressure sensor for this pump is described in U.S. Pat. No. 4,950,244, which is assigned to the same assignee as the present invention.

The pressure sensor disclosed in the above-referenced patent includes a rod that is in contact with the elastomeric membrane in the cassette at a pressure sensing location and is supported by two flexible supports that are widely spaced apart along a longitudinal axis of the rod. A strain gauge is mounted on the back of one of the flexible supports. As pressure changes in the passages of the cassette, and more particularly, at the pressure sensing location, the elastomeric membrane moves the pin axially. The movement of the pin causes a corresponding flexural displacement of the flexible supports. Flexural movement of the flexible support on which the strain gauge is mounted is detected by the strain gauge, producing a signal indicative of the pressure in the cassette at the pressure sensing location. Since the pressure sensor responds to a deflection of the flexible support indicative of fluid pressure, its response time to changes in pressure is limited by the dynamics of flexible support and movement of the elastomeric membrane.

Errors in the fluid pressure measured with the pressure sensor described above arise due to variations in the stiffness of the elastomeric membrane at varying pressures. Changes in pressure within the cassette cause substantial changes in the displacement of the elastomeric membrane. However, the stiffness of the elastomeric membrane changes as the membrane is stretched and displaced due to the fluid pressure. As a result, flexural movement of the flexible supports does not linearly track changing pressure in the cassette. These errors are not easily corrected in software, because the variation in stiffness of the elastomeric membrane as a function of pressure can differ from one cassette to another.

It will therefore be apparent that a different pressure sensor configuration is required, which is not subject to such errors. To minimize errors caused by variations in the stiffness of the elastomeric membrane, a pressure sensor is required that does not respond to flexural displacement of the elastomeric membrane. The pressure sensor must also compensate for differences in the stiffness of the elastomeric membrane in different cassettes. Further, the pressure sensor should be sufficiently compact in form so that it can monitor fluid pressures in a cassette at both proximal and distal locations relative to the pumping chamber. In addition, the pressure sensor should have a faster response time.

SUMMARY OF THE INVENTION

In accordance with the present invention, a pressure sensor is defined for monitoring a fluid pressure in a cavity enclosed on at least one side by an elastomeric membrane. The pressure sensor includes a pin having opposed first and second ends, the first end of the pin being adapted to contact the elastomeric membrane, subjecting the pin to an applied force caused by pressure in the cavity. A base that is adapted to mount the pressure sensor includes an upright portion. One end of a cantilevered arm is mounted to the base, and an opposite end of the arm extends free of the base and is disposed adjacent the second end of the pin. A pair of flat springs with planar surfaces are arranged in stacked array. The planar surfaces of these flat springs are generally parallel. Each flat spring is supported by the upright portion of the base, extending outwardly therefrom and then curving back toward the upright portion of the base. The ends of the flat springs are coupled to the pin at spaced-apart points along a longitudinal axis of the pin, elastically supporting the pin so that its second end is in contact with the cantilevered arm. A strain gauge is mounted on the cantilevered arm and produces a signal indicative of strain that is caused by stress. The stress in the cantilevered arm is due to a force exerted by the pin. The pin (and the flexible membrane) experiences substantially no displacement when responding to the pressure in the cavity. Consequently, the signal produced by the strain gauge is substantially independent of variations in stiffness of the elastomeric membrane.

The cantilevered arm is preferably mounted to a planar pad portion of the base, with the strain gauge mounted on a surface of the cantilevered arm adjacent to the planar pad portion; in the preferred embodiment, the cantilevered arm extends toward the upright portion of the base. In this embodiment, the pair of flat springs supporting the pin yield to axial displacement of the pin yet are sufficiently stiff to resist displacement of the pin in any other direction. The pressure sensor further comprises an elastomeric torus disposed where each flat spring is coupled to the pin, and a collar for compressing and extruding the elastomeric torus to secure the flat spring to the pin, precluding lateral movement of the pin relative to the flat springs.

The pressure sensor also includes control means, coupled to receive the signal produced by the strain gauge and to convert the signal into a digital signal indicating the fluid pressure in the cavity. The control means include compensating means for determining and compensating the pressure in the cavity for an offset in the signal that is caused by the characteristic stiffness of the elastomeric membrane. The compensating means determine the offset by causing a predefined volumetric change that correspondingly changes the pressure in the cavity. The change in pressure produces a change in the signal that indicates the relative stiffness of the flexible membrane, so that the appropriate offset can be applied.

As disclosed below, the base of the pressure sensor in the preferred embodiment is adapted to couple to a support in a cassette pump. The signal produced by the strain gauge is indicative of either a proximal pressure or a distal pressure;

the proximal and distal pressures are relative to a pumping chamber of a cassette used in the cassette pump.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
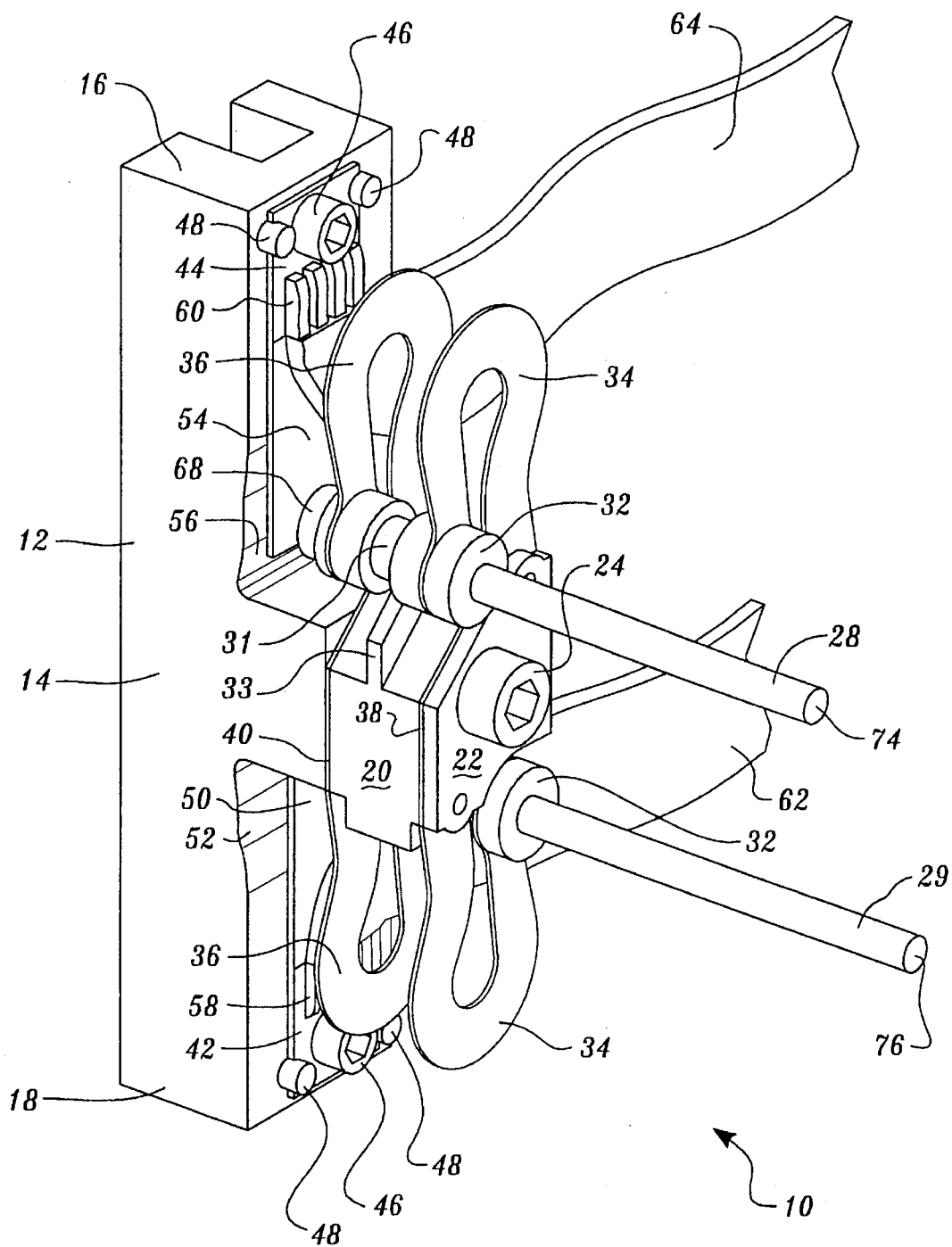
FIG. 1 is an isometric view of a pressure sensor that is able to monitor two different pressures, in accordance with the present invention.

As shown in FIG. 1, a pressure sensor 10 includes a generally T-shaped base 12; the base has a head portion 14, corresponding to the horizontal stroke of the "T," and a stem portion 20, which corresponds to the vertical stroke of the "T." Ends 16 and 18 of head portion 14 respectively support elements of the pressure sensor that produce two signals, each indicative of a pressure monitored at a different location.

Figure 3:
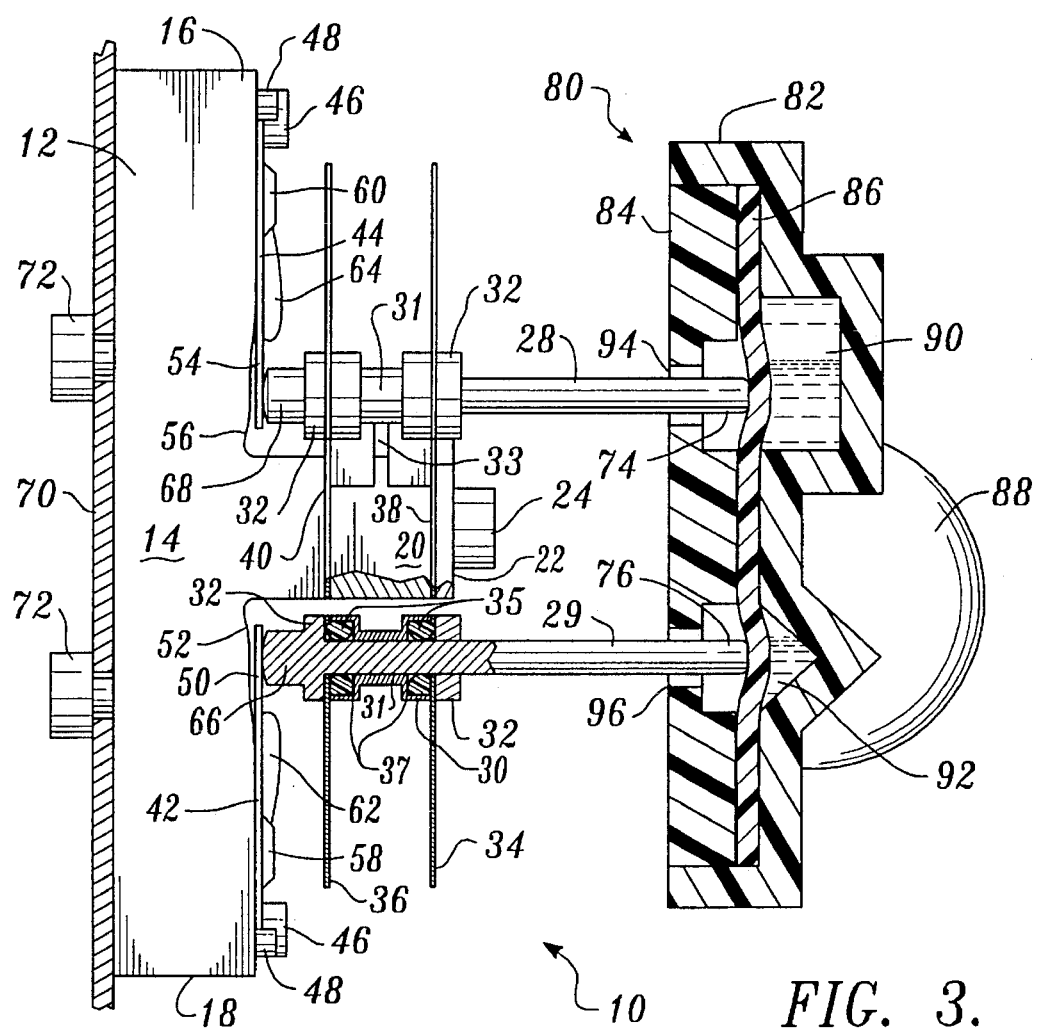
FIG. 3 is a partial, cut-away view of a disposable cassette, and a side elevational view of the pressure sensor of FIG. 1, partially cut-away, showing how the pressure sensor is used to monitor both proximal and distal fluid pressures in the cassette.

FIG. 3 shows pressure sensor 10, in a partially cut-away view. As clearly illustrated in FIGS. 1 and 6, each end of the block comprising stem 20 is angled to provide an increased clearance. A pin 28 is disposed adjacent the angled portion at one end of stem 20. Similarly, a pin 29 is disposed adjacent the other end of the stem. Around each of pins 28 and 29 is fitted a sleeve 30. A reduced diameter throat 31 is provided around each of the sleeves, centered midway along the longitudinal axis of the sleeve. A ridge 33, formed on the adjacent facing angled portion of stem 20, extends into throat 31 of each sleeve 30. Throat 31 is substantially wider than ridge 33 and normally should not contact it. Sleeves 30 serve as spacers, for mounting the pins to an S-shaped flat leaf spring 34 and a similarly S-shaped flat leaf spring 36. Pins 28 and 29 pass through apertures 43 disposed in the S-shaped flat leaf springs 34 and 36 and through sleeves 30, which are disposed between the springs, as shown in FIG. 3. The S-shaped flat leaf springs are thus arranged in spaced-apart array, extending generally parallel to each other, stacked above head 14.

Figure 5:
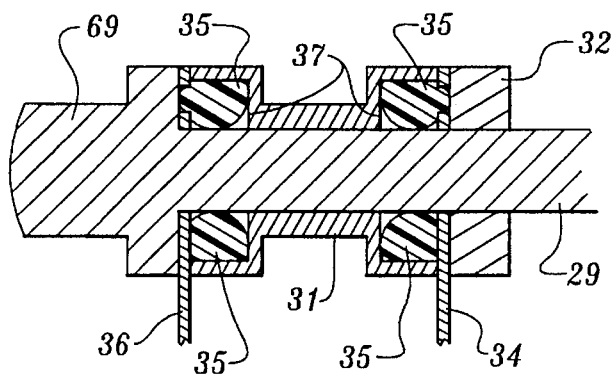
FIG. 5 is a cross-sectional view of one of the pins that conveys force from an elastomeric membrane to the pressure sensor, showing how the pin is compression clamped to two flat springs using extruded "O-rings"
Figure 6:
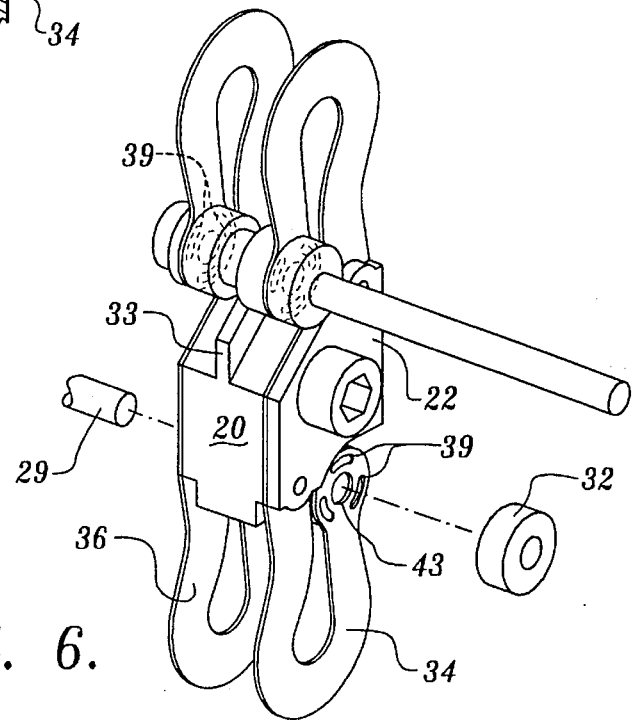
FIG. 6 is an isometric view of the pin and flat spring assembly, with an exploded view of one of the pins and a collar used to attach the pin to the flat springs.

An elastomeric "O-ring" 35 is disposed in an annular groove 37, formed at opposite ends of each sleeve 30. Pins 28 and 29 are coupled and compression clamped to the S-shaped flat leaf springs by collars 32, which are press fit over the pins, abutting against the S-shaped flat leaf springs and locking the ends of the S-shaped flat leaf springs against one of O-rings 35. Collars 32 that abut against the lower surface of S-shaped flat spring 36 may be integral with the lower end of their respective pins, as shown in the FIGS. 3 and 5, or may be separate, as are the collars that abut against the upper surface of S-shaped flat spring 34. The O-rings are compressed by the force exerted by collars 32, and are thus deformed or extruded into a plurality of arcuate slots 39 that are disposed in the ends of S-shaped flat leaf springs 34 and 36, spaced apart circumferentially around apertures 43, as shown in FIGS. 3, 5, and 6. Deformation of the O-rings in this manner securely couples the pins to the S-shaped flat springs. Thus, collars 32 and O-rings 35 retain pins 28 and 29 captive within the ends of the S-shaped flat leaf springs so that the pins do not move laterally within apertures 43, and sleeves 30 maintain the proper spacing between the S-shaped flat springs.

With reference to FIGS. 1 and 3, it will be noted that bolt 24 is used to mount S-shaped flat leaf springs 34 and 36 against opposite surfaces of the block comprising stem 20. A center 38 of S-shaped flat leaf spring 34 is disposed in contact with one surface of stem 20, and a center 40 of S-shaped flat leaf spring 36 is pressed in contact with the opposite surface of stem 20. A plate 22 is held against the upper surface of S-shaped flat spring 34 by bolt 24 to complete the mounting of the S-shaped flat springs on stem 20.

A cantilevered beam 42 is mounted on the upper surface of head 14, using a bolt 46 that passes through an aperture (not shown) that is disposed in the center and near one end of the cantilevered beam. Bolt 46 is threaded into end 18 of head 14. Cantilevered beam 42 is maintained generally in alignment with the edges of head 14 by stub pins 48, which are fitted into notches formed on each side of the cantilevered beam.

Similarly, an end of a cantilevered beam 44 is mounted to head 14 by another bolt 46 and stub pins 48, extending from end 16 of head 14 toward stem 20. Cantilevered beams 42 and 44 comprise relatively rigid (hardened steel) strips. A free end 50 of cantilevered beam 42 overlies a notch 52 relieved in the upper surface of head 14, adjacent one side of stem 20. Free end 50 is thus cantilevered relative to the planar surface of the head against which the opposite end of the cantilevered beam is securely mounted by bolt 46. In the same manner, a free end 54 of cantilevered beam 44 projects over a notch 56, which is relieved into the upper surface of head 14 adjacent the other side of stem 20.

Figure 4:
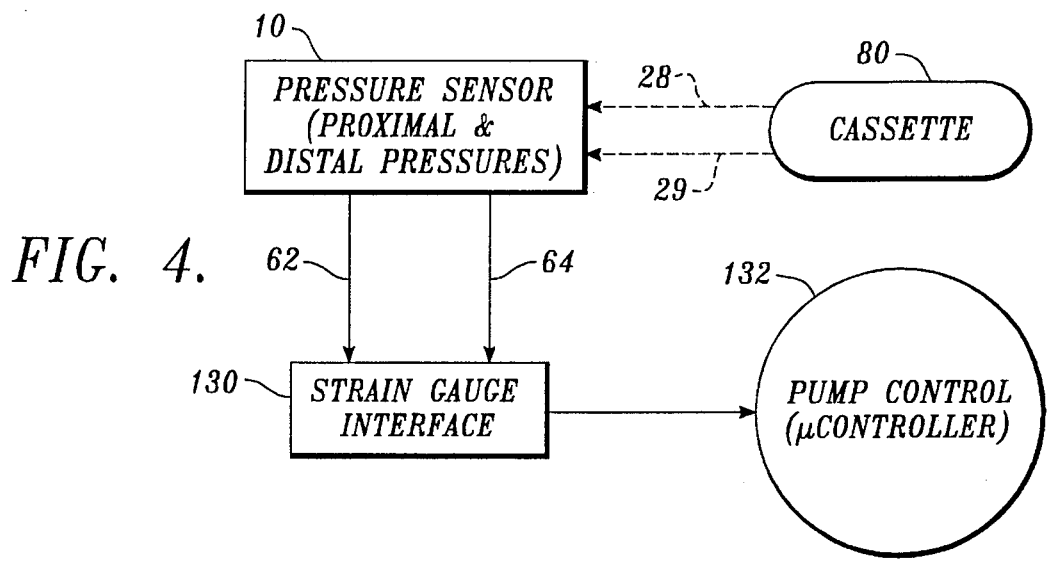
FIG. 4 is a block diagram of the pressure sensor, a strain gauge interface, the disposable cassette, and a pump controller, illustrating how these components cooperate in monitoring proximal and distal pressures in the cassette.

A strain gauge 58 is affixed (with epoxy) to the upper surface of cantilevered beam 42, positioned so as to detect stress in the cantilevered beam caused by any force exerted against free end 50. In response to the strain created by such stress, strain gauge 58 produces a signal indicative of the stress that is conveyed to a strain gauge interface 130 (shown in FIG. 4 and discussed below). On cantilevered beam 44 is affixed a strain gauge 60, mounted in an appropriate position so as to detect strain in cantilevered beam 44 caused by a stress exerted on free end 54. In response to such stress, strain gauge 60 produces a corresponding signal that is conveyed through a lead 64 to strain gauge interface 130 (FIG. 4).

An end 66 of pin 29 is supported in contact with free end 50 of cantilevered beam 42 by S-shaped flat leaf springs 34 and 36. In a similar manner, an end 68 of pin 28 is supported in contact with free end 54 of cantilevered beam 44. The parallel configuration of the S-shaped flat leaf springs constrain pins 28 and 29 to move freely only in an axial direction. However, the extent of the pins' ability to move reciprocally in their axial directions is limited in the preferred embodiment. Each of the pins can experience a maximum displacement of only about 0.007 inches before the free ends of the cantilevered beams bottom out against the adjacent surface of the base.

As shown in FIG. 3, pressure sensor 10 is mounted on a bracket 70 using bolts 72. In the preferred embodiment, bracket 70 is internally disposed within a cassette pump. During use of pressure sensor 10, a cassette 80 is inserted into the cassette pump and engaged with its driving mechanism. When the cassette is thus positioned, pressure sensor 10 can determine a proximal and distal pressure in the cassette as fluid is pumped through it for infusion into a patient. Only a few elements of cassette 80 are shown in FIG. 3; however, it is not necessary to disclose all of the details of the cassette since the cassette is not a part of the present invention. Cassette 80 includes an upper housing 82 that is formed of injection molded plastic, forming a plurality of passages and chambers that conduct fluid through the cassette. A lower housing 84 is joined to upper housing 82, thereby mounting an elastomeric membrane 86 between the two portions of the housing. As used herein, the terms "upper" and "lower" are purely arbitrary and are not intended to define an absolute spatial relationship of the components to which they are applied. Elastomeric membrane 86 comprises a thin sheet of elastomeric material, an upper surface of which defines one side of the fluid passages and chambers formed in upper housing 82.

In the cross section of cassette 80 shown in FIG. 3, a proximal fluid passage 90 is defined between elastomeric membrane 86 and upper housing 82. Similarly, a distal fluid passage 92 is defined by a different portion of the elastomeric membrane and the upper housing. Only cross sections of these passages within cassette 80 are shown. It should be noted that proximal fluid passage 90 is "proximal" or "upstream" relative to a pumping chamber 88. Similarly, distal fluid passage 92 is "distal" or "downstream" relative to pumping chamber 88. End 74 of pin 28 extends through an aperture 94 formed in lower housing 84 of the cassette, abutting against a lower surface of elastomeric membrane 86 at a point opposite the portion of the membrane that defines proximal fluid passage 90. Likewise, end 76 of pin 29 extends through an aperture 96 in the lower housing to abut against the lower surface of elastomeric membrane 86 at a point opposite the portion of the membrane that defines distal fluid passage 92. The points where ends 74 and 76 contact the elastomeric membrane are pressure measurement locations.

The pressure of a fluid within proximal fluid passage 90 develops a force that acts against elastomeric membrane 86 and via the elastomeric membrane is thus applied to end 74 of pin 28. Pin 28 transmits this force, which varies with the pressure of fluid within proximal fluid passage 90, against free end 54 of cantilevered beam 44, causing a corresponding stress in the cantilevered beam. The signal developed by strain gauge 60, which is attached to cantilevered beam 44, is thus indicative of the proximal fluid pressure within proximal fluid passage 90.

In similar fashion, the pressure of fluid within distal fluid passage 92 acts on elastomeric membrane 86 causing it to apply a force corresponding to the distal fluid pressure against end 76 of pin 29. Pin 29 transmits this force to free end 50 of cantilevered beam 42 developing a corresponding stress in the cantilevered beam. The signal produced by strain gauge 58, which is attached to cantilevered beam 42, is thus indicative of the distal fluid pressure in distal fluid passage 92.

Other components that are used for monitoring the proximal and distal pressures in a cassette are shown in FIG. 4. In this Figure, the dash lines extending from cassette 80 to pressure sensor 10 represent the forces transmitted through pins 28 and 29. The signals produced by the strain gauges comprising the pressure sensor are conveyed through leads 62 and 64 to strain gauge interface 130, which converts these analog signals into a corresponding digital signal that is input to a pump controller 132. Pump controller 132 includes a microcontroller (not separately shown) that responds to the digital proximal and distal pressures in controlling the cassette pump.

The microcontroller is programmed to carry out a procedure when the pump is initially energized or reset that determines an offset error resulting from an inherent stiffness of the elastomeric membrane. In this procedure, the pump controller causes a pumping plunger (not shown) to be advanced by a stepping motor (also not shown), applying a force against the elastomeric membrane that deflects it so as to change the volume of pumping chamber 88, and the pressure of the fluid within the pumping chamber. The stepping motor is moved a predefined number of steps, so that a corresponding defined change in the volume of the pumping chamber occurs. The defined change in the volume of the pumping chamber should cause a corresponding defined change in the pressure of the fluid in the pumping chamber. As the pressure of the fluid in the pumping chamber changes as a result of this procedure, pump controller 132 monitors the proximal fluid pressure signal produced by strain gauge 60. Based upon the digital proximal pressure signal produced by strain gauge interface 130, pump control 132 determines a durometer class for elastomeric membrane 86.

In the preferred embodiment of the present invention, the elastomeric membrane in a cassette can be classified in one of three durometer classes that are designated respectively as "soft," "medium," and "hard." The class assigned to the elastomeric membrane in this procedure to determine an offset correction is based upon the proximal pressure signal change caused as a known amount of fluid is displaced by the pump during the procedure. Calibration of the distal pressure sensor relative to that of the proximal pressure sensor occurs as the pump is in operation. The durometer class of the elastomeric membrane is assumed to be constant at all points on its surface.

The durometer class thus determined for the elastomeric membrane enables the pump control to assign an offset error correction for application to subsequent pressure measurements made on the cassette. Each time that the cassette is changed, or the cassette pump reenergized after being deactivated for a time, this process is repeated.

The above described procedure determines the offset error corrections required to compensate for the inherent stiffness of the elastomeric membrane. However, if the elastomeric membrane experiences significant displacement as the pressure changes, variations in the stiffness of the membrane with displacement, as well as the actual displacement of the elastomeric membrane, can cause an error in the signal produced by the pressure sensor. This problem was noted in a prior art pressure sensor 100, shown in FIG. 2. An advantage of pressure sensor 10 over pressure sensor 100 is that pressure sensor 10 responds to changes in stress, which result from changes in load applied through the pins to cantilevered beams 42 and 44—not displacement. Since displacement of the elastomeric membrane with pressure is so small, the only significant change in load applied to the pins and to the cantilevered beams occurs solely as a result of changes in pressure and not because of any significant displacement of the elastomeric membrane. As the proximal or distal pressure changes, pins 28 and 29 experience very little displacement, and the elastomeric membrane at the proximal and distal fluid pressure measurement locations similarly experience very little displacement. In contrast, in prior art pressure sensor 100, a substantial displacement of the elastomeric membrane occurs with increasing pressure and its signal is subject to a substantial non-linearity error. Furthermore, because cantilevered beams 42 and 44 are relatively stiffer and do not experience significant flexural displacement, the response time of pressure sensor 10 is substantially faster than the prior art pressure sensor.

To understand why prior art pressure gauge 100 is susceptible to non-linearity and other errors related to flexural movement due to pressure, its components and operation must first be described. Prior art pressure sensor 100 includes a generally L-shaped base 102. Base 102 supports an upper elongate flat spring 108 and a lower elongate flat spring 110. Elongate flat springs 108 and 110 are mounted in spaced-apart array, generally extending parallel to each other above base 102. The ends of these elongate flat springs are mounted on each side of a block 104 by a bolt 106 that is threaded into the base.

A pin 112 is supported by the flat elongate flat springs. Pin 112 is mounted to the elongate flat springs on each side of a spacer 114 and is held in place by collars 116. Pin 112 extends generally perpendicular to the flat elongate springs so that when a cassette 80' (an earlier design that is slightly different than cassette 80) is mounted in a cassette pump (not shown) in which pressure sensor 100 is disposed, an end 120 of pin 112 contacts a flexible membrane 86' within the cassette. Pin 112 extends through an aperture 118 formed in a lower housing 84' to contact the flexible membrane. Flexible membrane 86' defines one side of a cavity 98 through which fluid flows in the cassette. The pressure of the fluid within cavity 98 displaces elastomeric membrane 86', causing a corresponding displacement of pin 112. A strain gauge 122 is attached directly to lower elongate flat spring 110, adjacent block 104. Strain gauge 122 responds to the bending of flat elongate spring 110 caused by the displacement of pin 112, producing a signal that is conveyed through a lead 124. This signal is indicative of the fluid pressure in cavity 98.

Figure 2:
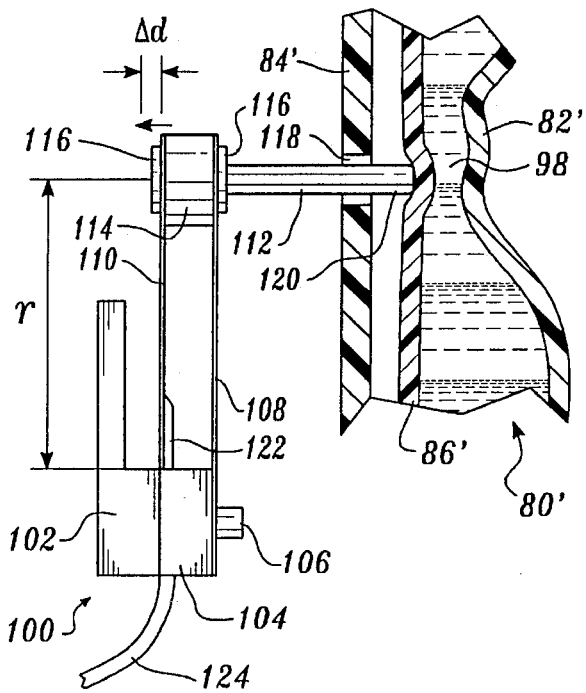
FIG. 2 is a cut-away, partial view of a fluid passage in a disposable cassette that is used to pump fluid and side elevational view of a prior art pressure sensor that monitors fluid pressure in the cassette.

With reference to FIG. 2, it will be noted that flat elongate springs 108 and 110 deflect a distance Ad in response to the pressure of fluid within cavity 98. The maximum displacement Ad over the full range of pressure sensed by pressure sensor 100 is greater than 0.030 inches and in some versions of the prior art pressure sensor, greater than 0.080 inches. Because of the design of prior art pressure sensor 100, the rather substantially greater displacement required of elastomeric membrane 86' and pin 112, compared to that in the present invention introduce a significant non-linearity error due to the variation in the stiffness of the elastomeric membrane with changing pressure. Elongate flat springs 108 and 110 support pin 112 at a distance R from mounting block 104 in pressure sensor 100 that is relatively long compared to the distance between pins 28 and 29 and stem 20 in pressure sensor 10. Consequently, in the prior art pressure sensor, strain gauge 122 responds to the displacement of pin 112 and elastomeric membrane 86', which produces a corresponding bending or deflection of flat elongate spring 110. In contrast, strain gauges 58 and 60 in pressure sensor 10 respond to stress in the cantilevered beams, with a substantially zero displacement of flexible membrane 86. In fact, the cantilevered beams in pressure sensor 10 can only deflect a maximum of 0.007" because of the minimal relief provided by notches 52 and 56 in head 14. The stiffness of the cantilevered beam is sufficient to limit the deflection of flexible membrane at the pressure measurement locations to less than this maximum displacement over the full range of pressure monitored. Because of the elastomeric membrane does not experience more than this de minimus displacement, the signals produced by pressure sensor 10 have a predictable, substantially linear slope.

Although the present invention has been described in connection with a preferred embodiment, it will be understood by those of ordinary skill in the art that many modifications can be made thereto within the scope of the claims that follow. Accordingly, it is not intended that the scope of the invention in any way be limited by the above description, but that it be determined entirely by reference to the claims that follow.

The invention in which an exclusive right is claimed is defined by the following:

1. Apparatus for monitoring a fluid pressure in a cavity, said apparatus comprising:

(a) an elastomeric membrane that encloses said cavity on at least one side, said elastomeric membrane varying in stiffness; and (b) a pressure sensor disposed adjacent the elastomeric membrane and including:

(i) a pin having opposed first and second ends, the first end of the pin contacting the elastomeric membrane, subjecting the pin to an applied force caused by pressure in the cavity;

(i) a base used to mount the pressure sensor and including an upright portion;

(iii) a cantilevered arm having one end mounted to the base and an opposite end extending free and disposed adjacent the second end of the pin;

(iv) a pair of flat springs arranged in stacked array, each flat spring having planar surfaces that are arranged generally in parallel with the planar surfaces of the other flat spring, each flat spring being supported by the upright portion of the base, extending outwardly therefrom, and then curving back toward the upright portion of the base, ends of the flat springs being coupled to the pin at spaced-apart points along a longitudinal axis of the pin, said pair of flat springs elastically supporting the pin so that its second end is in contact with the cantilevered arm; and (v) a strain gauge mounted on the cantilevered arm, said strain gauge producing a signal indicative of strain in the cantilevered arm caused by stress, the stress being due to a force exerted on said cantilevered arm by the pin in response to the fluid pressure in the cavity, said pin experiencing a displacement sufficiently small when responding to the pressure in the cavity so that said signal produced by the strain gauge is substantially independent of the varying stiffness of the elastomeric membrane, thereby substantially eliminating a non-linear error in the signal that would otherwise be caused by the varying stiffness of the elastomeric membrane.

2. The apparatus of claim 1, wherein the base portion includes a planar pad portion, and wherein the cantilevered arm is mounted to the planar pad portion of the base, with the strain gauge mounted on a surface of the cantilevered arm adjacent to the planar pad portion.

3. The apparatus of claim 2, wherein the cantilevered arm is mounted on the base so that it extends toward the upright portion of the base.

4. The apparatus of claim 1, further comprising an elastomeric torus disposed where each flat spring is coupled to the pin, and a collar for compressing the elastomeric torus to secure the flat spring to the pin.

5. The apparatus of claim 1, wherein the pair of flat springs supporting the pin resist displacement of the pin in any direction not aligned with a longitudinal axis of the pin.

6. The apparatus of claim 1, further comprising control means, coupled to receive the signal produced by the strain gauge and to convert the signal into a digital signal indicating the fluid pressure in the cavity.

7. The apparatus of claim 6, wherein the control means include compensating means for determining and compensating the pressure in the cavity for an offset in the signal caused by the stiffness of the elastomeric membrane.

8. The apparatus of claim 7, wherein the compensating means determine the offset by causing a predefined change in the pressure in the cavity, said change in the pressure producing a change in the signal that indicates the stiffness of the elastomeric membrane.

9. The apparatus of claim 7, wherein the base of the pressure sensor couples the pressure sensor to a support in a cassette pump, the signal produced by the strain gauges being indicative of one of a proximal pressure and a distal pressure of a cassette used in the cassette pump, the proximal and distal pressures being monitored at locations respectively upstream and downstream of a pumping chamber of the cassette.

10. A pressure sensor for sensing fluid pressure applied to an elastomeric membrane at two discrete points, said elastomeric membrane being characterized by variations in its stiffness, comprising:

(a) a base that is generally T-shaped, having a stem portion and a head portion, said head portion of said base being used to mount the pressure sensor adjacent to the elastomeric membrane;

(b) a pair of pins disposed on opposite sides of the stem portion of the base, each of said pins including opposed first and second ends, the first end of each pin contacting the elastomeric membrane at different ones of the discrete points enabling each of the pins to experience a force corresponding to a fluid pressure applied to the elastomeric membrane at said discrete points;

(c) a pair of cantilevered arms, each cantilevered arm having one end mounted to the base and an opposite end extending free of the base, adjacent the second end of a different one of the pins;

(d) a pair of flat springs stacked one above the other, extending outwardly from opposite sides of the stem in generally spaced-apart, parallel array, said flat springs curving back toward the stem and elastically supporting the pins on the opposite sides of the stem so that the second end of each pin is in contact with a different one of the cantilevered arms, said flat springs being coupled to the pins at spaced-apart points along longitudinal axes of the pins; and (e) a pair of strain gauges, each strain gauge being mounted on a different one of the cantilevered arms, each strain gauge producing a signal indicative of strain in said cantilevered arm caused by stress, said stress being due to a force transmitted by one of the pins from the elastomeric membrane to the cantilevered arm in response to the fluid pressure applied to the elastomeric membrane, each of said pins experiencing a maximum displacement when responding to the force exerted by the elastomeric membrane, which is substantially less than a displacement that would produce a non-linear error in the signal produced by each strain gauge due to the variations in the stiffness of the elastomeric membrane.

11. The pressure sensor of claim 10, wherein the head portion includes a planar pad portion; and wherein each of the cantilevered arms is mounted to the planar pad portion of the head portion, each of said pair of strain gauges being mounted on a surface of a different one of the cantilevered arms, adjacent to a different one of the planar pad portions.

12. The pressure sensor of claim 11, wherein each of the cantilevered arms is mounted on the base so that it extends toward the stem of the base.

13. The pressure sensor of claim 10, wherein the flat springs include apertures through which the pins extend, further comprising compression clamps that fixedly couple the pins to the flat springs so as to substantially eliminate radial movement of the pins within the apertures.

14. The pressure sensor of claim 10, wherein the cantilevered arms resist displacement of the pins, enabling the pressure sensor to dynamically respond to fluid pressures acting on the elastomeric membrane, at the two discrete points.

15. The pressure sensor of claim 10, further comprising control means, coupled to receive the signals produced by the strain gauges and to convert the signals into indications of a magnitude of fluid pressure acting on the elastomeric membrane, at the two discrete points.

16. The pressure sensor of claim 15, wherein the control means include compensating means for determining and compensating the pressure acting on the elastomeric membrane for any offsets caused by the characteristic stiffness of the elastomeric membrane.

17. The pressure sensor of claim 16, wherein the compensating means determine the offsets by causing a predefined change in the pressure acting upon the elastomeric membrane at the discrete points, and then monitoring corresponding changes in the signal produced by the strain gauges.

18. The pressure sensor of claim 16, wherein the base of the pressure sensor couples the pressure sensor to a support in a cassette pump, the signals produced by the strain gauges being indicative of a proximal and a distal pressure at measurement locations disposed relative to a pumping chamber of a cassette used in the cassette pump.

19. A pressure sensor for sensing a fluid pressure in a cavity at least partially defined by a substantially planar elastomeric membrane that is characterized by variations in stiffness, the fluid pressure acting on the elastomeric membrane to produce a force corresponding to the pressure in the cavity, said pressure sensor comprising:

(a) a supporting base;

(b) a cantilevered beam that is mounted to the supporting base;

(c) a pin for transmitting force exerted by the elastomeric membrane due to fluid pressure;

(d) means for elastically supporting the pin in contact with the cantilevered beam and the elastomeric membrane, for enabling the pin to transmit the force exerted by the elastomeric membrane in response to the fluid pressure in the cavity and substantially independent of a non-linear error due to the variation in the stiffness of the elastomeric membrane; and (e) a strain gauge that is mounted on the cantilevered beam to sense stress on the cantilevered beam caused by the force transmitted from the elastomeric membrane through the pin, producing a signal indicative of the pressure in the cavity, said signal having substantially no error due to variations in the stiffness of the elastomeric membrane as a function of its displacement.

20. A pressure sensor for sensing a fluid pressure in a cassette pump, where a cassette used in said pump includes an elastomeric membrane that is substantially planar at a point a fluid pressure is monitored by the pressure sensor, the elastomeric membrane being characterized by variations in its stiffness, said pressure sensor comprising:

a base for mounting the pressure sensor adjacent to the cassette; and force sensing means that are mounted on the base to couple to the elastomeric membrane, said force sensing means producing a signal indicative of the fluid pressure in the cassette and including means that substantially eliminate an error in said signal caused by the variations in the stiffness of the elastomeric membrane.

21. The pressure sensor of claim 20, wherein the force sensing means include:

(a) a cantilevered beam extending from the base;

(b) a strain gauge mounted to the cantilevered beam to sense stress thereon, said strain gauge producing the signal; and (c) means for transmitting a force from the elastomeric membrane to the cantilevered beam, said cantilevered beam being sufficiently stiff that it limits displacement of the elastomeric membrane to a value below which the non-linear error caused by the variations in the stiffness of the elastomeric membrane is substantially eliminated, when the cantilevered beam is subjected to a predefined maximum force corresponding to a maximum design pressure for the pressure sensor.

* * * * *

UNITED STATES PATENT AND TRADEMARK OFFICE
CERTIFICATE OF CORRECTION

PATENT NO. : 5,554,115
DATED : September 10, 1996
INVENTOR(S) : V. Stanton Thomas et al.

It is certified that error appears in the above-indentified patent and that said Letters Patent is hereby corrected as shown below:

| Column | Line | |
|---|---|---|
| 4 | 60 | "mourned" should read --mounted-- |
| 7 | 52 | "Ad" should read --$\Delta$d-- |
| 7 | 54 | "Ad" should read --$\Delta$d-- |

Signed and Sealed this

Eighteenth Day of March, 1997

Attest:

BRUCE LEHMAN

*Attesting Officer*   Commissioner of Patents and Trademarks